United States Patent [19]

Wettling et al.

[11] Patent Number: 5,396,006
[45] Date of Patent: Mar. 7, 1995

[54] PREPARATION OF ALKENES AND OF CYCLOPENTANE AND CYCLOHEXANE

[75] Inventors: Thomas Wettling, Limburgerhof; Jochem Henkelmann, Mannheim, both of Germany

[73] Assignee: BASF Aktiengesellschaft, Ludwigshafen, Germany

[21] Appl. No.: 136,938

[22] Filed: Oct. 18, 1993

[51] Int. Cl.⁶ ............................ C07C 1/28; C07C 11/02
[52] U.S. Cl. ..................................... 585/359; 585/641; 585/642
[58] Field of Search ..................... 585/359, 642, 641

[56] References Cited

U.S. PATENT DOCUMENTS

| 2,380,995 | 8/1945 | Roehow . | |
|---|---|---|---|
| 2,381,000 | 8/1945 | Patnode . | |
| 2,553,797 | 5/1951 | Thompson | 260/590 |
| 3,450,782 | 6/1969 | Connor | 260/666 |
| 4,435,379 | 3/1984 | Olson et al. | 423/472 |

FOREIGN PATENT DOCUMENTS

| 2515002 | 4/1983 | France . |
|---|---|---|
| 235630 | 5/1988 | Germany . |

OTHER PUBLICATIONS

Houben-Weyl, Methoden der Org. Chem. vol. V/1b, Thieme Verlag 1972, pp. 182 to 190.

*Primary Examiner*—Asok Pal
*Assistant Examiner*—Bekir L. Yildirim
*Attorney, Agent, or Firm*—Keil & Weinkauf

[57] ABSTRACT

Preparation of alkenes as well as of cyclopentane and cyclohexane from the corresponding vicinal dichloro and dibromo alkanes and from α,ω-Dichloropentane and α,ω-dibromopentane and α,ω-dichlorohexane and α,ω-dibromohexane respectively, in which these starting compounds are caused to react with with silicon.

7 Claims, No Drawings

PREPARATION OF ALKENES AND OF CYCLOPENTANE AND CYCLOHEXANE

The present invention relates to a novel process for the preparation of alkenes as well as of cyclopentane and cyclohexane from the corresponding vicinal dichloro and dibromo alkanes and from α,ω-dichloro or α,ω-dibromo alkanes or α,ω-dichloro or α,ω-dibromohexane respectively.

Chlorinated and brominated hydrocarbons are generally disposed of by incineration. Such combustion processes are uneconomical from an engineering point of view on account of the off-gas purification required.

U.S. Pat. No. 4,435,379 teaches a process for the reaction of chlorinated hydrocarbons with various metal oxides to produce CO, $CO_2$ and the corresponding metal chlorides. The requisite temperatures are above 700° C. and thus involve high energy consumption.

The reaction of monochloro alkanes or monochloro aromatics with silicon has acquired industrial significance as Rochow process in particular for the preparation of methylchloro and phenylchloro silanes (U.S. Pat. No. 2,380,995).

The reaction of silicon with α,ω-dihalo alkanes having from 1 to 4 carbon atoms leads, as taught by U.S. Pat. NO. 2,381,000, to α,ω-bis-silyl compounds.

It is known to be possible to dehalogenate vicinal aliphatic dihalides with metals such as sodium, lithium, and magnesium and primarily zinc. The corresponding metal halides are also formed as by-products (Houben-Weyl, *Methoden der Org. Chem.*, Vol. V/1 b, Thieme Verlag 1972, pp. 182 to 190).

It is an object of the present invention to provide a process which constitutes a simple way of preparing alkenes as well as cyclopentane and cyclohexane by dehalogenation of the corresponding dichloro or dibromo compounds. Other valuable products are desirably produced in this process in addition to the said hydrocarbons.

Accordingly, we have found a process for the preparation of alkenes as well as of cyclopentane and cyclohexane from the aforementioned starting compounds, wherein these starting compounds are caused to react with silicon.

Dichloro and dibromo compounds are suitable starting materials for the process of the invention, of which the dichloro compounds are preferred.

The starting compounds are primarily by-products produced when chlorination or bromination of hydrocarbons is carried out on an industrial scale, such as, in particular, propane, butane, pentane, and hexane.

The process is particularly significant for the dehalogenation of vicinal dichloro and dibromo alkanes such as 2,3-dichlorobutane and, in particular, 1,2-dichloropropane.

Other starting compounds are α,ω-dichloropentane and α,ω-dibromopentane as well as dichloro and dibromo hexanes, of which 1,6-dichlorohexane is preferred. The compounds can carry some other inert substituents such as alkyl groups.

Silicon or silicon in the form of its alloys are used as dehalogenating agents. The use of relatively pure silicon having a silicon content of, say, from 98% to more than 99.9 wt % is preferred. In addition, industrial crude silicon having a silicon content of from about 90% to 98 wt % can be used. Silicon alloys such as ferrosilicon having a silicon content of preferably more than 50 wt % silicon are also suitable.

By-products are obtained when use is made of slightly impure silicon or silicon alloys, but in relatively small amounts, so that the purification of the reaction mixture is not unduly impaired.

Since the reaction is a heterogeneous reaction, the more finely divided the silicon is the better are the results obtained. It is thus advisable to use silicon or silicon alloys in the form of powders or granules having an average particle size of from approximately 0.05 to 0.5 mm.

The silicon can be used in stoichiometric amounts, i.e. 1 equivalent of silicon for every 4 equivalents of halogen. An excess of silicon is recommendable, however, for the purpose of accelerating the reaction. Unconverted silicon can be isolated and used in subsequent batches.

It has been found to be particularly advantageous to add copper(II) chloride to the silicon. The amounts suitable for this purpose are usually in the range of from 0.1 to 20 wt %, based on the silicon used. Heating to from 250° to 300° C. has given good results for activation of this additive prior to commencement of the reaction.

Other metals or metal compounds such as zinc oxide and manganic oxide can also be used as additives or alternatively main group elements such as sulfur or compounds of main group elements such as phosphorus pentoxide. The amounts used are generally in the range of from 0.001 to 1 wt %, based on silicon.

The process may be carried out in various modifications.

It is industrially particularly advantageous, in the case of halogenated hydrocarbons which are gaseous at the reaction temperature and under standard pressure, to pass them in gaseous form through a fluidized bed of silicon powder. The products can then be condensed and separated in known manner.

Halogenated hydrocarbons which are liquid or solid at the reaction temperature may be simply heated with silicon with removal, by distillation, of volatile reaction products.

The reaction temperature is usually in the range of from 100° to 600° C. and preferably in the range of from 150° to 350° C. and more preferably from 180° to 320° C.

The reaction is usually carried out under standard pressure, but it can be carried out under subatmospheric pressure or under elevated pressure if desired. The process can be carried out continuously or batchwise.

The reaction is preferably carried out in the absence of oxygen, as otherwise oxidation of the organic compounds and also, at high temperatures, of the silicon may occur. The reaction can be carried out under a blanket of protective gas such as a noble gas or nitrogen.

Chlorine-containing or bromine-containing silanes are formed as reaction products, in the preferred embodiments predominantly silicon tetrachloride.

The process of the invention allows for the conversion of vicinal dichloro and dibromo alkanes to the corresponding olefins, which may be used directly for further syntheses. It also allows for the formation of cyclopentane and cyclohexane from the corresponding open-chain α,ω-dihalo alkanes, which are used, e.g. as solvents. The bromo or chloro silanes formed in the process have a wide range of industrial uses.

EXAMPLES

Example 1

Preparation of propene from 1,2-dichloropropane 140 g (5 mol) of silicon powder (average particle size: 0.2 mm, purity: 99%) and 14 g (10 wt %) of copper(II) chloride were heated for 1 h at a temperature of 265° C. 115 g (1 mol) of 1,2-dichloropropane in the nitrogen stream were introduced over a period of 3 h at 230° C. into a fluidized bed of the pretreated silicon/CuCl. The gaseous reaction products were condensed and distilled. 20.8 g (0.5 mol) of propene were isolated (selectivity 87%) and also 45 g (0.27 mol) of silicon tetrachloride (selectivity 93%) and 49.5 g of unconverted 1,2-dichloropropane. The conversion was 57%.

Example 2

Preparation of butenes from 2,3-dichlorobutane 55 g (0.44 mol) of 2,3-dichlorobutane were caused to react in a manner similar to that described in Example 1 at a temperature of 250° C. over a period of 2 h. The condensates were analyzed by gas chromatography. There were obtained 12% of silicon tetrachloride, 27% of butenes, 23% of monochlorobutenes, and 16% of 2,3-dichlorobutane (all of the percentages stated are percentages by area (GC)). Unidentified products were also produced.

Example 3

Preparation of cyclohexane from 1,6-dichlorohexane 54 g (0.35 mol) of 1,6-dichlorohexane were caused to react over a period of 2 h in a manner similar to that described in Example 1 at a temperature of 280° C. The condensates were examined using gas chromatography methods. There were obtained 32% of trichlorosilane, 2% of silicon tetrachloride, 23% of 6-chlorohex-1-ene, 8% of cyclohexane, and 18% of 1,6-dichlorohexane (all percentages stated are percentages by area (GC)). Unidentified products were also produced.

We claim:

1. A process of preparing alkenes, comprising the step of dehalogenating a vicinal dichloro or dibromo alkane by reacting said alkane with silicon.

2. A process of preparing cyclopentane, comprising the step of dehalogenating an $\alpha,\omega$-dichloro or a, $\alpha,\omega$-dibromo pentane by reacting said pentane with silicon.

3. A process of preparing cyclohexane, comprising the step of dehalogenating an $\alpha,\omega$-dichloro or $\alpha,\omega$-dibromo hexane by reacting said hexane with silicon.

4. The process of claim 1, wherein copper(II) chloride is present as an additive.

5. The process of claim 2, wherein copper(II) chloride is present as an additive.

6. The process of claim 3, wherein copper(II) chloride is present as an additive.

7. The process of claim 1, wherein said alkane is 1,2-dichloropropane.

* * * * *